US010960152B2

(12) United States Patent
Zuber et al.

(10) Patent No.: US 10,960,152 B2
(45) Date of Patent: Mar. 30, 2021

(54) NICOTINE PARTICLE CAPSULE

(71) Applicant: PHILIP MORRIS PRODUCTS S.A., Neuchatel (CH)

(72) Inventors: Gerard Zuber, Froideville (CH); Nicolo Volpe, Lausanne (CH)

(73) Assignee: Philip Morris Products S.A., Neuchâtel (CH)

( * ) Notice: Subject to any disclaimer, the term of this patent is extended or adjusted under 35 U.S.C. 154(b) by 351 days.

(21) Appl. No.: 16/064,177

(22) PCT Filed: Dec. 19, 2016

(86) PCT No.: PCT/IB2016/057792
§ 371 (c)(1),
(2) Date: Jun. 20, 2018

(87) PCT Pub. No.: WO2017/109678
PCT Pub. Date: Jun. 29, 2017

(65) Prior Publication Data
US 2019/0001084 A1      Jan. 3, 2019

(30) Foreign Application Priority Data

Dec. 24, 2015   (EP) .................................... 15202712
Nov. 30, 2016   (EP) .................................... 16201580

(51) Int. Cl.
*A61M 15/00*   (2006.01)
*A61M 15/06*   (2006.01)
(Continued)

(52) U.S. Cl.
CPC ....... *A61M 15/0035* (2014.02); *A61K 31/465* (2013.01); *A61K 47/183* (2013.01);
(Continued)

(58) Field of Classification Search
CPC ................ A61M 15/00; A61M 15/003; A61M 15/0035; A61M 15/0041; A61M 15/06; A61M 15/08; A24F 40/20; A24F 42/20; A24F 47/002; A61P 25/00; A61P 25/26; A61P 43/00; A61K 31/465
See application file for complete search history.

(56) References Cited

U.S. PATENT DOCUMENTS 4,064,878 A   12/1977   Lundquist
4,069,819 A   1/1978    Valentini et al.
(Continued)

FOREIGN PATENT DOCUMENTS

CN   1424909 A      6/2003
CN   101888867 A    11/2010
(Continued)

OTHER PUBLICATIONS

International Search Report and Written Opinion, issued by the European Patent Office, as the International Searching Authority, for PCT/IB2016/057792, dated Mar. 9, 2017; 11 pgs.
(Continued)

*Primary Examiner* — Joseph D. Boecker
(74) *Attorney, Agent, or Firm* — Mueting Raasch Group

(57) ABSTRACT

A capsule containing particles including nicotine wherein a single aperture extends through the capsule.

16 Claims, 1 Drawing Sheet

Figure 1:
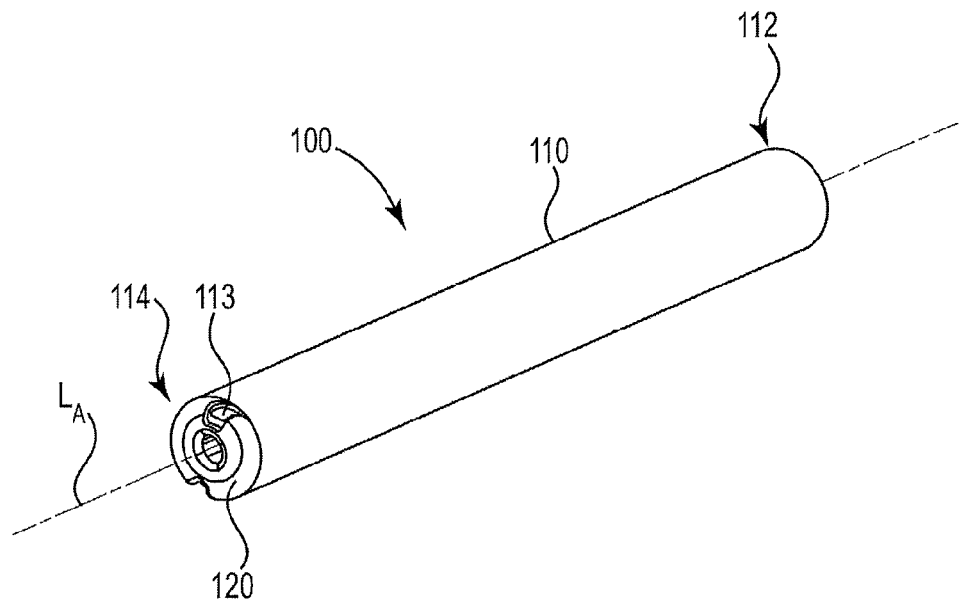
Figure 2:
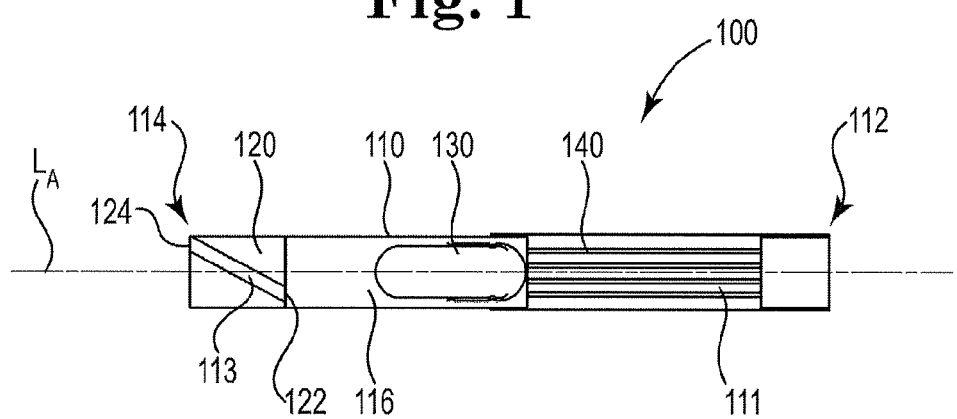

(51) Int. Cl.
*A61K 31/465* (2006.01)
*A61K 47/18* (2017.01)
*A24F 47/00* (2020.01)

(52) U.S. Cl.
CPC ...... *A61M 15/003* (2014.02); *A61M 15/0021* (2014.02); *A61M 15/06* (2013.01); *A24F 47/002* (2013.01); *A61M 2202/064* (2013.01)

(56) References Cited

U.S. PATENT DOCUMENTS

| | | | |
|---|---|---|---|
| 4,695,274 | A | 9/1987 | Fox |
| 4,735,217 | A | 4/1988 | Gerth et al. |
| 4,790,305 | A | 12/1988 | Zoltan |
| 4,995,385 | A | 2/1991 | Valentini et al. |
| 5,673,686 | A * | 10/1997 | Villax ............... A61M 15/0028 128/203.15 |
| 5,746,227 | A | 5/1998 | Rose et al. |
| 6,102,036 | A | 8/2000 | Slutsky et al. |
| 8,813,759 | B1 | 8/2014 | Horian |
| 2003/0015195 | A1 | 1/2003 | Haaije de Boer |
| 2003/0165436 | A1 | 9/2003 | Staniforth et al. |
| 2003/0180227 | A1 | 9/2003 | Staniforth |
| 2004/0156792 | A1 * | 8/2004 | Tarara ................. A61K 9/0075 424/46 |
| 2004/0206350 | A1 | 10/2004 | Alston et al. |
| 2008/0241255 | A1 | 10/2008 | Rose et al. |
| 2011/0220234 | A1 | 9/2011 | Haas |
| 2012/0145150 | A1 | 6/2012 | Donovan et al. |
| 2014/0088044 | A1 | 3/2014 | Rigas et al. |
| 2014/0088045 | A1 | 3/2014 | Rigas et al. |
| 2014/0130800 | A1 | 5/2014 | Seeney et al. |
| 2015/0136131 | A1 | 5/2015 | Holakovsky et al. |
| 2017/0071248 | A1 * | 3/2017 | Stenzler ............ A61M 15/0035 |
| 2017/0135397 | A1 * | 5/2017 | Buehler ............ A61M 15/0035 |
| 2018/0147371 | A1 * | 5/2018 | Stenzler ................ A24F 47/002 |

FOREIGN PATENT DOCUMENTS

| | | | | |
|---|---|---|---|---|
| EP | 0333334 | A2 | 9/1989 | |
| EP | 2 399 637 | A1 | 12/2011 | |
| GB | 2415597 | A * | 1/2006 | ............ A24D 3/048 |
| GB | 2 461 008 | A | 12/2009 | |
| RU | 2460677 | C2 | 9/2012 | |
| WO | WO 91/01656 | A1 | 2/1991 | |
| WO | WO 2007/061987 | A2 | 5/2007 | |
| WO | WO 2009/075794 | A1 | 6/2009 | |
| WO | WO 2015166344 | A1 | 5/2015 | |
| WO | WO 2015/166344 | A1 | 11/2015 | |
| WO | WO 2015/166350 | A2 | 11/2015 | |
| WO | WO 2015/193498 | A1 | 12/2015 | |
| WO | WO-2015193498 | A1 * | 12/2015 | ........ A61M 15/0036 |
| WO | WO-2015197863 | A1 * | 12/2015 | ............ B65D 53/00 |

OTHER PUBLICATIONS

Written Opinion, issued by the European Patent Office, as the International Preliminary Examining Authority, for PCT/IB2016/057792, dated Jan. 8, 2018; 6 pgs.

International Preliminary Report on Patentability, issued by the European Patent Office, as the International Preliminary Examining Authority, for PCT/IB2016/057792, dated Apr. 16, 2018; 18 pgs.

Cohen et al., "GRAS Flavoring Substances," 27. *GRAS Flavoring Substances. Food Technology for Flavoring Extract Manufacturers Association*, 2015:69(8):40-59.

* cited by examiner

NICOTINE PARTICLE CAPSULE

This application is the § 371 U.S. National Stage of International Application No. PCT/IB2016/057792, filed 19 Dec. 2016, which claims the benefit of EP Patent Application No. 15202712.4, filed 24 Dec. 2015 and EP Patent Application No. 16201580.4, filed 30 Nov. 2016, the disclosures of which are incorporated by reference herein in their entireties.

This disclosure relates to a nicotine particle capsule a single aperture. The nicotine particle capsule may be a suitable consumable to be used in a dry powder inhaler.

Dry powder inhalers are not always fully suitable to provide dry powder to the lungs at inhalation or air flow rates that are within conventional smoking regime inhalation or air flow rates. Dry powder inhalers often strive to provide an entire dry powder dose in a single breath.

It would be desirable to provide a nicotine particle article that may be combined with a dry powder inhaler to provide particles comprising nicotine to the lungs at inhalation or air flow rates that are within conventional smoking regime inhalation or air flow rates. It would also be desirable to provide a nicotine particle article that may release the particles comprising nicotine over at least 5 puffs or at least 10 puffs.

This disclosure is directed to a capsule containing particles comprising nicotine, wherein a single aperture extends through the capsule. The single aperture may be sized to provide a fractional amount of particles comprising nicotine with each puff or inhalation when utilized with a dry powder inhaler.

The capsule may be suitable to be used in a dry powder inhaler. The capsule may be part of an article suitable to be used in a dry powder inhaler. The capsule may be a modular component of a multi-use dry powder inhaler. The capsule may be easily replaceable within the multi-use dry powder inhaler. Once consumed, the capsule or article may be removed from the multi-use dry powder inhaler and discarded.

Advantageously, the single aperture may be sized to provide a uniform entrainment of a portion or a fraction of nicotine particles from the capsule over five or more, or ten or more, or 15 or more "puffs" by a consumer.

The capsule described herein may provide a dry powder (comprising nicotine particles) to the lungs at inhalation or air flow rates that are within conventional smoking regime inhalation or air flow rates when combined with a dry powder inhaler. A consumer may take a plurality of "puffs" where each "puff" delivers a fractional amount of dry powder contained within a capsule contained within the capsule cavity. This may mimic the ritual of conventional smoking.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R.L. & Oser, B.L., Food Technology, February 1965 pg 151-197, and in the GRAS flavoring substances 27 S.M. Cohen et al., Food Technology Aug. 2015 pg. 40-59, and intervening GRAS Flavoring Substances publications 4 to 26. For the purpose of this disclosure, nicotine is not considered as a flavourant or flavour.

The capsule may be combined with a piercing element or piercing device to form the single aperture in the capsule. The piercing element or piercing device may be separated from or not separated from a portion of the inhaler article. A plurality of the capsules or articles comprising the capsule may be combined with a dry powder inhaler to form a kit.

The capsule includes one and only one aperture extending through the capsule. The capsule does not comprise more than one aperture extending through the capsule. Air may flow into and out of the same single aperture.

The capsule contains particles comprising nicotine. The capsule may also contain particles which do not comprise nicotine. The particles comprising nicotine and the particles which do not comprise nicotine may constitute a dry powder.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

The single aperture may have a diameter from about 0.1 mm to 4 mm or from 0.2 mm to 2 mm or from about 0.5 mm to about 1.5 mm, or from about 0.6 mm to about 1 mm, or from about 0.7 mm to about 0.9 mm, or about 0.8 mm. The single aperture may have an open surface area from about 0.1 $mm^2$ to about 2 $mm^2$ or from about 0.2 $mm^2$ to about 1 $mm^2$, or from about 0.4 to about 0.6 $mm^2$.

The ratio of the diameter of the single aperture to the mass median aerodynamic diameter of the particles comprising nicotine may be from about 50 to about 3200, or from about 100 to about 1600, or from about 200 to about 800, or from about 300 to about 600.

The ratio of the diameter of the single aperture to the mean diameter of the dry powder may be from about 5 to about 320, or from about 10 to about 160, or from about 20 to about 80, or from about 30 to about 60.

The single aperture may be incident with a longitudinal axis of the capsule. When the capsule is placed in dry powder inhaler and pierced, airflow through the dry powder inhaler may cause the capsule to rotate about the longitudinal axis of the capsule.

The capsule may define an internal volume referred as the internal volume of the capsule. The internal volume of the capsule may be from 0.02 ml to about 3 ml or from about 0.1 ml to about 0.9 ml or from about 0.2 ml to about 0.45 ml, or from about 0.25 ml to about 0.3 ml. The single aperture may have an open surface area of from about 0.7 $mm^2$ to about 7 $mm^2$ per ml of internal volume of the capsule or from about 1 $mm^2$ to about 2 $mm^2$ per ml of internal volume of the capsule.

The capsule may contain from about 10 mg to about 200 mg or from about 20 mg to about 100 mg or from 40 mg to 70 mg of dry powder. The capsule may contain from about 10mg to about 200 mg or from about 20 mg to about 100 mg or from 40 mg to 70 mg of particles comprising nicotine.

The article or capsule may be disposed in a capsule cavity of a dry powder inhaler. The capsule cavity may define a cylindrical space configured to contain the capsule (that may have an obround shape). The capsule cavity may have a substantially uniform or uniform diameter along the length of the capsule cavity. The capsule cavity may have a substantially cylindrical or cylindrical cross-section along the length of the capsule cavity. The configuration of the capsule cavity relative to the capsule may allow the capsule to rotate with stability within the capsule cavity. The longitudinal axis of the capsule may rotates with stability about the longitudinal axis of the inhaler body during inhalation.

Stable rotation refers to the longitudinal axis of the inhaler body being substantially parallel with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over five or more, or ten or more, or 15 or more "puffs" by a consumer.

The capsule cavity may have a cavity inner diameter, orthogonal to the longitudinal axis, and the capsule has a capsule outer diameter. The capsule outer diameter may be in a range from about 80% to about 99% of the cavity inner diameter, or capsule outer diameter may be in a range from about 85% to about 95% of the cavity inner diameter, or capsule outer diameter may be about 90% of the cavity inner diameter. The capsule outer diameter may be in a range from about 5.4 mm to about 6.4 mm and the cavity inner diameter may be in a range from about 6 mm to about 7 mm, or the capsule outer diameter may be in a range from about 5.7 mm to about 6.1 mm and the cavity inner diameter may be in a range from about 6.4 mm to about 6.8 mm, or the capsule outer diameter may be about 5.85 mm and the cavity inner diameter may be about 6.6 mm.

The capsule cavity may be bounded on an upstream side by the end cap and bounded on a downstream side by a porous support element. The end cap and porous support element cooperate to contain the capsule longitudinally within the capsule cavity. The porous support element may fill the inner diameter of the elongated inhaler body. The porous support element may allow air flow to exhibit a uniform airflow along the cross-section of the elongated inhaler body through the porous support element. The porous support element may function as a diffuser to reduce turbulence effects or edge effects and ensure or maintain the desired air flow pattern through the capsule cavity.

The porous support element may have a length that extends along the longitudinal axis a distance from about 20 mm to about 40 mm, or from about 22 mm to about 35 mm, or from about 25 mm to about 30 mm, or about 27 mm. The porous support element may have an outer diameter sufficient to form a friction fit with the inner diameter of the inhaler body. The porous support element may have an outer diameter in a range from about 5 mm to about 10 mm, or from about 6 mm to about 9 mm, or 6.5 mm to about 8.5 mm, or about 7.5 mm.

The porous support element may define a filter element. The filter element may be formed of a network of fibres. The network of fibres may be a nonwoven fibre element. The porous support element may be a plug of filtration material. Fibers forming the porous support element may be derived from polylactic acid. Fibers forming the porous support element may be cellulose acetate. The filter element may be a plug of cellulose acetate or a plug of polylactic acid. The porous element may comprise a plastic mesh. The plastic mesh may have holes of from about 1 $mm^2$ to about 4 $mm^2$ or of about 2 $mm^2$.

The capsule may be sealed within the inhaler article prior to consumption. The inhaler article may be contained within a sealed or airtight container or bag. The inhaler article may include one or more peelable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler to form the single aperture. The capsule may formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 or a size 3 capsule.

A separate piercing element, such as a metal or rigid needle, may form a single aperture through the capsule received in the capsule cavity. The piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 5 inhalations or "puffs", or at least about 10 inhalations or "puffs", or at least about 15 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred as powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 10 micrometres or less, or 5 micrometers or less, or in a range from about 1 micrometer to about 3 micrometres.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as, L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about 50 micrometres or greater. The powder system may have at least about 40% or at least about 60%, or at least about 80%, by weight of the flavour of the powder system comprised in particles having a particle size in a range from about 50 micrometer to about 150 micrometres. The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

As described above, the particles comprising nicotine and the particles comprising flavour may each have reduced adhesion forces that result in a stable particle formulation where the particle size of each component does not substantially change when combined.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

Rotation of the single aperture capsule within the inhaler body may aerosolize the nicotine particles or powder system and may assist in maintaining a free flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 Umin or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler containing the nicotine capsule with only a single aperture may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 1 is a perspective view of an illustrative inhaler article.

FIG. 2 is a cross-sectional schematic diagram of the illustrative inhaler article of FIG. 1 along the longitudinal axis.

FIG. 3 is a schematic diagram end view of a nicotine consumable capsule with the single aperture.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 and FIG. 2 illustrate an exemplary inhaler article 100. FIG. 2 is a cross-sectional schematic diagram of the illustrative inhaler article of FIG. 1 along the longitudinal axis. The inhaler article 100 includes a body 110 extending along a longitudinal axis $L_A$ from a mouthpiece end 112 to a distal end 114 and a capsule cavity 116 defined within the body 110. A mouthpiece air channel 111 extends from the capsule cavity 116 to the mouthpiece end 112. An end cap 120 is disposed within the distal end 112 and extends to the capsule cavity 116. The end cap 120 extends from an end cap distal end 124 to an end cap inner end 122. The end cap 120 includes an air channel 113 extending from the end cap distal end 124 to the end cap inner end 122. The air channel 113 is non-parallel with the longitudinal axis $L_A$.

The end cap inner end 122 and a porous support element 140 bound the capsule cavity 116. A capsule 130 is disposed within the cavity 116. The capsule 130 contains particles comprising nicotine. The end cap 120 and the porous support element 140 cooperate to contain the capsule 130 longitudinally within the capsule cavity 116. The mouthpiece end 112 is illustrated having a recessed end where the body 110 bounds an open space at the mouthpiece end 112. Alternatively the porous support element 140 can extend to the mouthpiece end 112 to fill the entire mouthpiece end 112.

Figure 3:
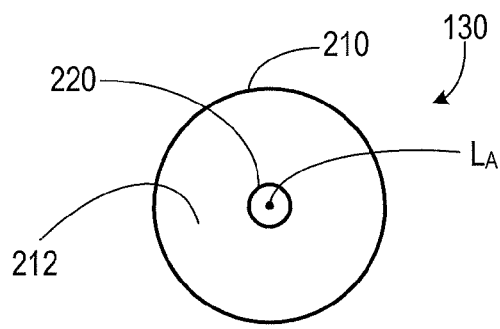

FIG. 3 is a schematic diagram end view of a nicotine capsule 130 with only a single aperture 220. The single aperture 220 may extend though the capsule body 210 at an end portion 212 of the capsule body 210. The single aperture 220 may be incident with a longitudinal axis of the capsule 130 and incident with the longitudinal axis $L_A$ of the inhaler body 110.

A separate piercing element (not shown) may be utilized by a consumer to pierce the nicotine capsule 130 and form the single aperture 220 through the piercing channel shown in FIG. 1 in the end cap 120 along the longitudinal axis $L_A$. The piercing element may be withdrawn from the single aperture 220. A consumer may then utilize the nicotine capsule 130 in an inhaler device 100.

The invention claimed is:

1. A capsule containing particles comprising nicotine salt and having a mass median aerodynamic diameter from about 0.5 micrometers to about 4 micrometers, and particles comprising flavor and having a mass median aerodynamic diameter from 50 micrometers to 150 micrometers, the capsule defining an internal volume,
wherein only a single aperture having a diameter from about 0.5 mm to about 1.5 mm extends through the capsule and is sized to provide a fraction amount of the particles comprising nicotine salt and the particles comprising flavor, at conventional smoking regime air flow rates of less than about 5 L/min once a piercing element used to form the single aperture is withdrawn from the single aperture.

2. The capsule according to claim 1, wherein the ratio of the diameter of the single aperture to the mass median aerodynamic diameter of the particles comprising nicotine is from about 200 to about 800.

3. The capsule according to claim 1, wherein the particles comprising nicotine salt comprise an amino acid.

4. The capsule according to claim 1, wherein the single aperture has an open surface area of from about 0.2 mm$^2$ to about 1 mm$^2$.

5. The capsule according to claim 1, wherein the internal volume of the capsule is from about 0.2 ml to about 0.45 ml.

6. The capsule according to claim 1, wherein the single aperture has an open surface area in a range from about 0.7 mm$^2$ to about 7 mm$^2$ per ml of internal volume of the capsule.

7. The capsule according to claim 1, wherein the capsule contains from about 10 mg to about 200 mg of dry powder.

8. The capsule according to claim 1, wherein the single aperture is incident with a longitudinal axis of the capsule.

9. A dry powder inhaler comprising a capsule according to claim 1.

10. The dry powder inhaler according to claim 9, wherein the capsule is disposed in a capsule cavity configured to allow the capsule to rotate with stability within the capsule cavity.

11. The capsule according to claim 1, wherein the particles comprising nicotine comprise leucine or L-leucine.

12. The capsule according to claim 2, wherein the particles comprising nicotine comprise leucine or L-leucine.

13. The capsule according to claim 1, wherein the nicotine comprises nicotine salt comprises nicotine pyruvate, nicotine citrate, nicotine aspartate, nicotine lactate, nicotine bitartrate, nicotine salicylate, nicotine fumarate, nicotine monopyruvate, or nicotine glutamate.

14. A dry powder inhaler comprising a capsule according to claim 12.

15. A capsule containing particles comprising nicotine salt and particles comprising flavor, the capsule defining an internal volume,
wherein only a single aperture extends through the capsule and is sized to provide a fraction amount of the particles comprising nicotine salt and the particles comprising flavor during an inhalation at conventional smoking regime air flow rates of less than about 5 L/min once a piercing element used to form the single aperture is withdrawn from the single aperture, the capsule providing from 5 to 10 inhalations of 0.1 mg to 3 mg nicotine particles per inhalation,
the particles comprising nicotine having a mass median aerodynamic diameter from about 0.5 micrometers to about 4 micrometers and the particles comprising flavor having a mass median aerodynamic diameter from 50 micrometers to 150 micrometers.

16. The capsule of claim 15, wherein the nicotine salt comprises nicotine pyruvate, nicotine citrate, nicotine aspartate, nicotine lactate, nicotine bitartrate, nicotine salicylate, nicotine fumarate, nicotine monopyruvate, or nicotine glutamate.

* * * * *